United States Patent
Ueno

(10) Patent No.: US 9,946,817 B2
(45) Date of Patent: Apr. 17, 2018

(54) METHOD FOR CALCULATING INTERACTION POTENTIAL BETWEEN FILLER PARTICLES IN POLYMERIC MATERIAL

(71) Applicant: SUMITOMO RUBBER INDUSTRIES, LTD., Kobe-shi, Hyogo (JP)

(72) Inventor: Shinichi Ueno, Kobe (JP)

(73) Assignee: SUMITOMO RUBBER INDUSTRIES, LTD., Kobe-Shi, Hyogo (JP)

(*) Notice: Subject to any disclaimer, the term of this patent is extended or adjusted under 35 U.S.C. 154(b) by 968 days.

(21) Appl. No.: 14/313,405

(22) Filed: Jun. 24, 2014

(65) Prior Publication Data

US 2014/0379313 A1    Dec. 25, 2014

(30) Foreign Application Priority Data

Jun. 25, 2013  (JP) .................................. 2013-133001

(51) Int. Cl.
  *G06F 17/50*  (2006.01)
  *G06F 19/00*  (2018.01)

(52) U.S. Cl.
  CPC ...... *G06F 17/5009* (2013.01); *G06F 17/5018* (2013.01); *G06F 19/704* (2013.01)

(58) Field of Classification Search
  None
  See application file for complete search history.

(56) References Cited

U.S. PATENT DOCUMENTS

2014/0067350 A1* 3/2014 Ueno .................. G06F 17/5009
                                                    703/6

OTHER PUBLICATIONS

Frischknecht et al., "Density functional theory for inhomogeneous polymer systems. I. Numerical methods", The Journal of Chemical Physics, vol. 117, No. 22, Dec. 2002, pp. 10385-10397.*
Bulacu, "Molecular Dynamics Studies of Entangled Polymer Chains", PhD Thesis, University of Groningen, The Netherlands, Jan. 2008, 152 pages.*
Extended European Search Report dated Aug. 8, 2014, for European Application No. 14172318.9.
Marla et al., "Simulation of Interaction Forces between Nanoparticles in the Presence of Lennard-Jones Polymers: Freely Adsorbing Homopolymer Modifiers," Langmuir, vol. 21, No. 1, Jan. 1, 2005, pp. 487-497.
Müller-Plathe, "Scale-Hopping in Computer Simulations of Polymers," Soft Materials, vol. 1, No. 1, 2003, pp. 1-31.
Raos et al., "Computational Experiments on Filled Rubber Viscoelasticity: What is the Role of Particle-Particle Interactions?," Macromolecules, vol. 39, No. 19, Sep. 1, 2006, pp. 6744-6751.

* cited by examiner

*Primary Examiner* — Omar Fernandez Rivas
*Assistant Examiner* — Herng-Der Day
(74) *Attorney, Agent, or Firm* — Birch, Stewart, Kolasch & Birch, LLP

(57) ABSTRACT

A method for calculating an interaction potential between filler particles in a polymeric material by using a computer is disclosed. The method comprises: arranging filler models and polymer models in a virtual space; calculating a free energy in the virtual space based on a mean field theory; obtaining parameters of the Lennard-Jones potential by approximating the free energy to the Lennard-Jones potential.

2 Claims, 9 Drawing Sheets

METHOD FOR CALCULATING INTERACTION POTENTIAL BETWEEN FILLER PARTICLES IN POLYMERIC MATERIAL

BACKGROUND OF THE INVENTION

The present invention relates to a method for calculating an interaction potential between filler particles in a polymeric material, more particularly to a method for determining parameters of the Lennard-Jones potential between the filler particles.

In recent years, in order to develop or design rubber compositions, various computer simulation methods for evaluating properties of a composite of a polymeric material and filler have been proposed.

In such a simulation method, for example, filler models of filler particles are defined, and the Lennard-Jones potential $U_{LJ}$ given by the following equation (1) (namely, an interaction potential between two filler models) is defined between the filler models.

$$U_{LJ}(r_{ij}) = 4\varepsilon_{LJ}\left\{\left(\frac{\sigma_{LJ}}{r_{ij}}\right)^{12} - \left(\frac{\sigma_{LJ}}{r_{ij}}\right)^{6}\right\} \quad \text{Equation (1)}$$

wherein
$r_{ij}$ is the distance between two filler models,
$\varepsilon_{LJ}$ is a coefficient for the intensity of the potential between the filler models, and
$\sigma_{LJ}$ corresponds to the diameter of the filler models.

Heretofore, the above-mentioned parameters $\sigma_{LJ}$ and $\varepsilon_{LJ}$ have been determined by an operator based on his/her intuition and experience, therefore, it is difficult to perform the simulation with high accuracy.

SUMMARY OF THE INVENTION

It is therefore, an object of the present invention to provide a method for calculating an interaction potential between filler particles in a polymeric material, by which parameters of the interaction potential, in particular, the Lennard-Jones potential between the filler particles can be determined by the use of a computer though a calculation.

According to the present invention, a method for calculating an interaction potential between filler particles in a polymeric material by using a computer, comprises:
a process in which a filler model of each of the filler particles is defined,
a process in which a polymer model of each of macromolecular chains of the polymeric material is defined,
a process in which the filler models and the polymer models are set in a predetermined virtual space,
a process in which a free energy in the virtual space is calculated based on the mean field theory, and
a process in which, by approximating the free energy to the Lennard-Jones potential, parameters of the Lennard-Jones potential are obtained.

In the present invention, therefore, the parameters of the Lennard-Jones potential can be determined based on the free energy in the virtual space. This is based on findings of the present inventor obtained through experiments, namely, the free energy in the virtual space calculated based on the mean field theory approximates the interaction potential between the filler models. Thus, the parameters can be determined without the need for human intuition and experience. As a result, it is possible to perform the simulation with high accuracy.

The calculating method according to the present invention may further include the following features (1)-(3):
(1) the filler models are a pair of the filler models, and the process for calculating the free energy comprises
a step (a) in which, by abutting the filler models, a minimum value Es of the free energy is calculated, and
a step (b) in which, by separating the filler models from each other, a maximum value Fm of the free energy is calculated;
(2) the filler models have a certain diameter, and the parameters of the Lennard-Jones potential include
a parameter $\varepsilon_{LJ}$ relating to the strength of a repulsive force exerted between the filler models by the Lennard-Jones potential, and
a parameter $\sigma_{LJ}$ corresponding to the diameter of the filler models, and
the process for obtaining the parameter $\varepsilon_{LJ}$ and parameter $\sigma_{LJ}$ comprises
a step (c) in which the parameter $\varepsilon_{LJ}$ is obtained from the difference between the maximum value Fm and the minimum value Fs of the free energy, and
a step (d) in which the parameter $\sigma_{LJ}$ is obtained from a distance between the filler models which abut each other to calculate the minimum value Fs of the free energy;
(3) a $\chi$ parameter relating to an interaction between a filler model and a polymer model is set in a range of from 0.0 to 10.0.

DESCRIPTION OF THE PREFERRED EMBODIMENTS

Embodiments of the present invention will now be described in detail in conjunction with the accompanying drawings.

The method for calculating an interaction potential between filler particles in a polymeric material according to the present invention (abbreviated to "calculating method") is carried out by the use of a computer 1.

Here, the filler may be any kind of filler including carbon black, silica, alumina and the like. The polymeric material may be any kind of polymer including rubber, elastomer, resin and the like.

Figure 1:
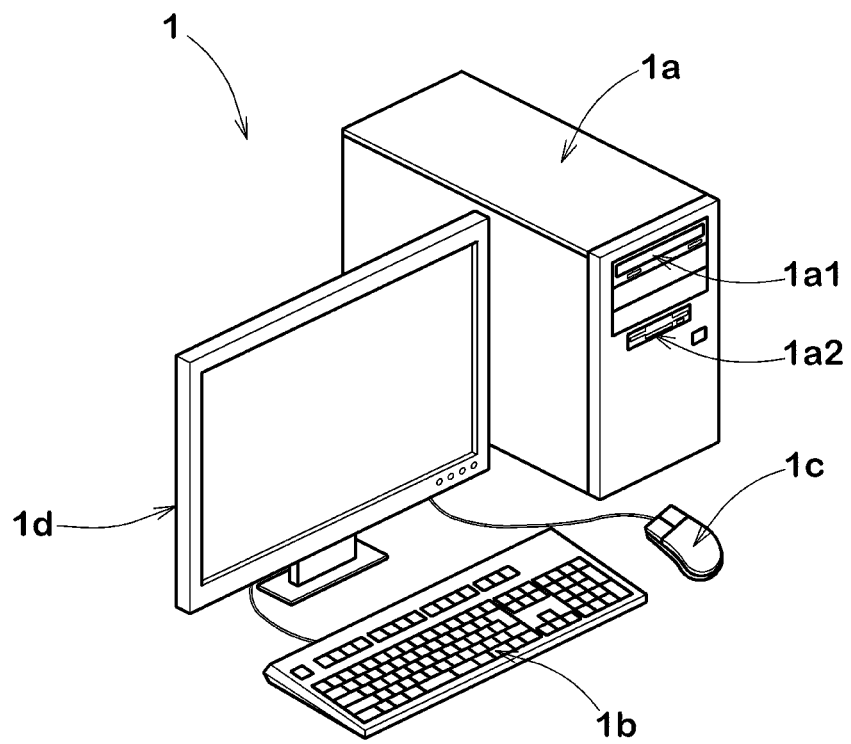
FIG. 1 shows a computer for implementing a method for calculating an interaction potential between filler particles in a polymeric material according to the present invention.

As shown in FIG. 1 for example, the computer 1 implementing the calculating method comprises a main body 1a, a keyboard 1b, a mouse 1c and a display 1d. The main body 1a comprises an arithmetic processing unit (CPU), memory, storage devices such as magnetic disk, disk drives 1a1 and 1a2 and the like. In the storage device, programs/software for carrying out the calculating method is stored.

Figure 2:
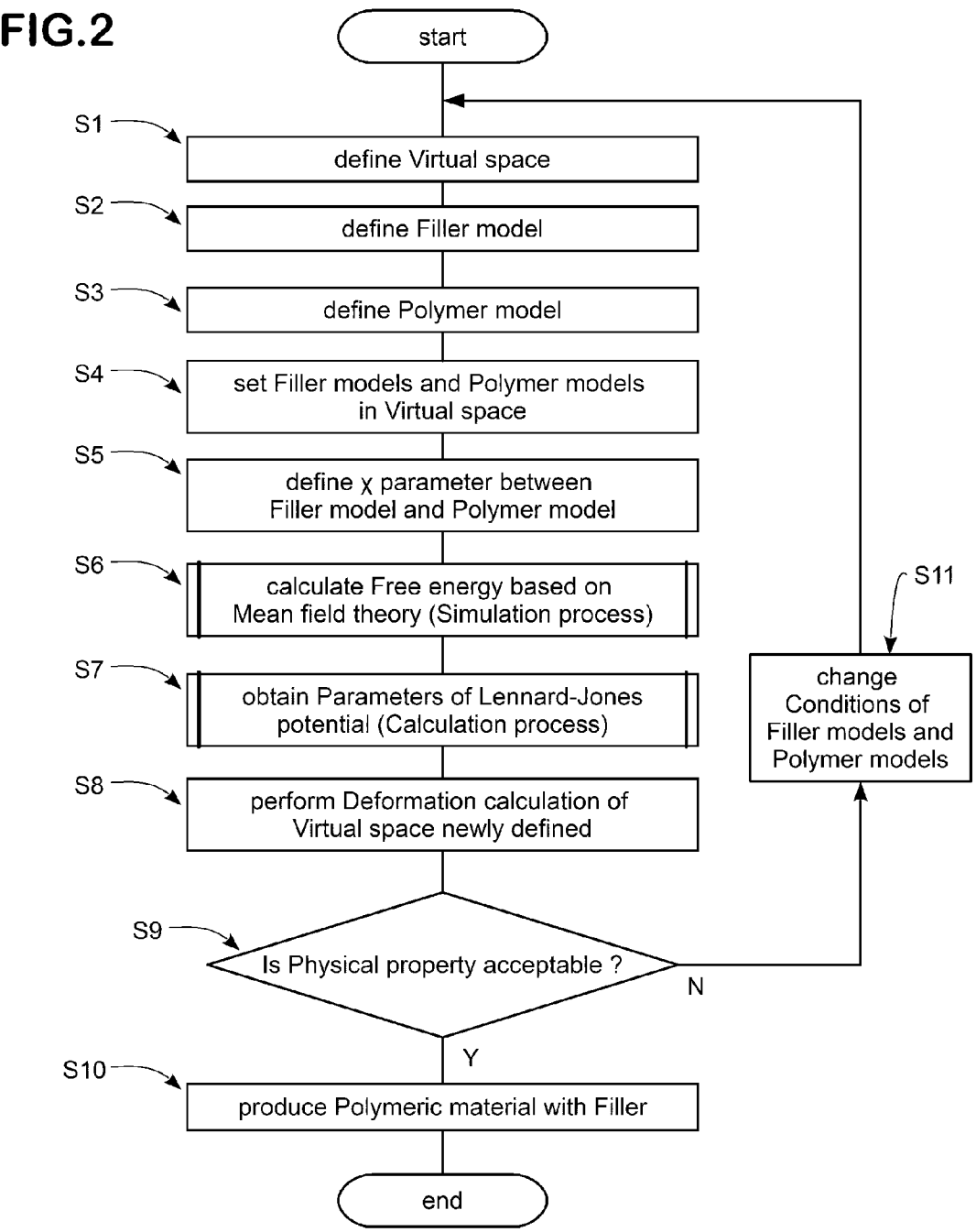
FIG. 2 is a flow chart of the calculating method according to the present invention.

FIG. 2 shows a flow chart of the calculating method as an embodiment of the present invention. The entire process thereof will be explained hereunder.

* Process S1

Figure 3:
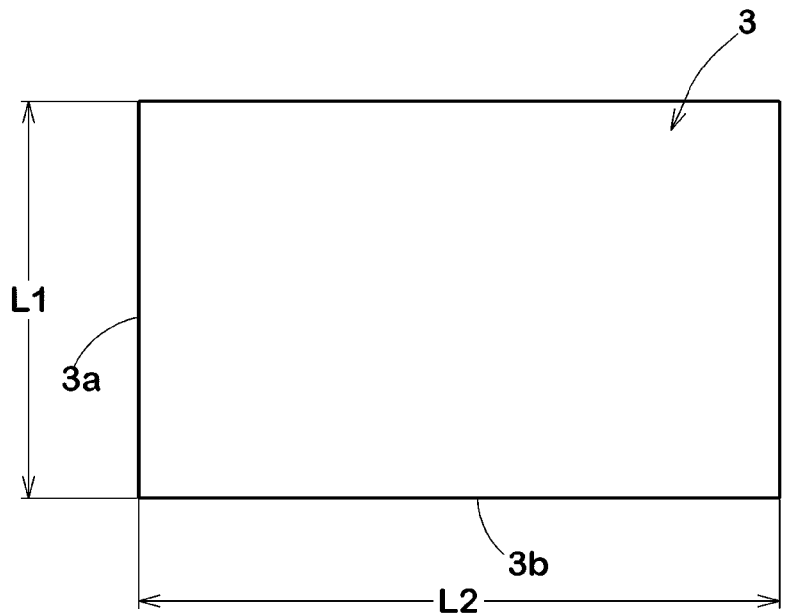
FIG. 3 is a diagram showing a virtual space used to obtain parameters of the Lennard-Jones potential.

In the process S1, a virtual space 3 is defined. In this embodiment, as shown in FIG. 3, the virtual space 3 is two-dimensional and has a horizontally long rectangular shape. on the respective sides 3a and 3b surrounding the virtual space 3, periodic boundary conditions are defined. The length L1 of the sides 3a and the length L2 of the sides 3b may be set arbitrarily, but it is preferable that the length L1 and the length L2 are set in a range of not less than 2 times, more preferably not less than 10 times the radius of gyration of the filler models 4 and the polymer model 6 (shown in FIG. 4). Data about such virtual space 3 are stored in the computer 1.

* Process S2

In the process S2, a filler model of each of the filler particles is defined.

Figure 4:
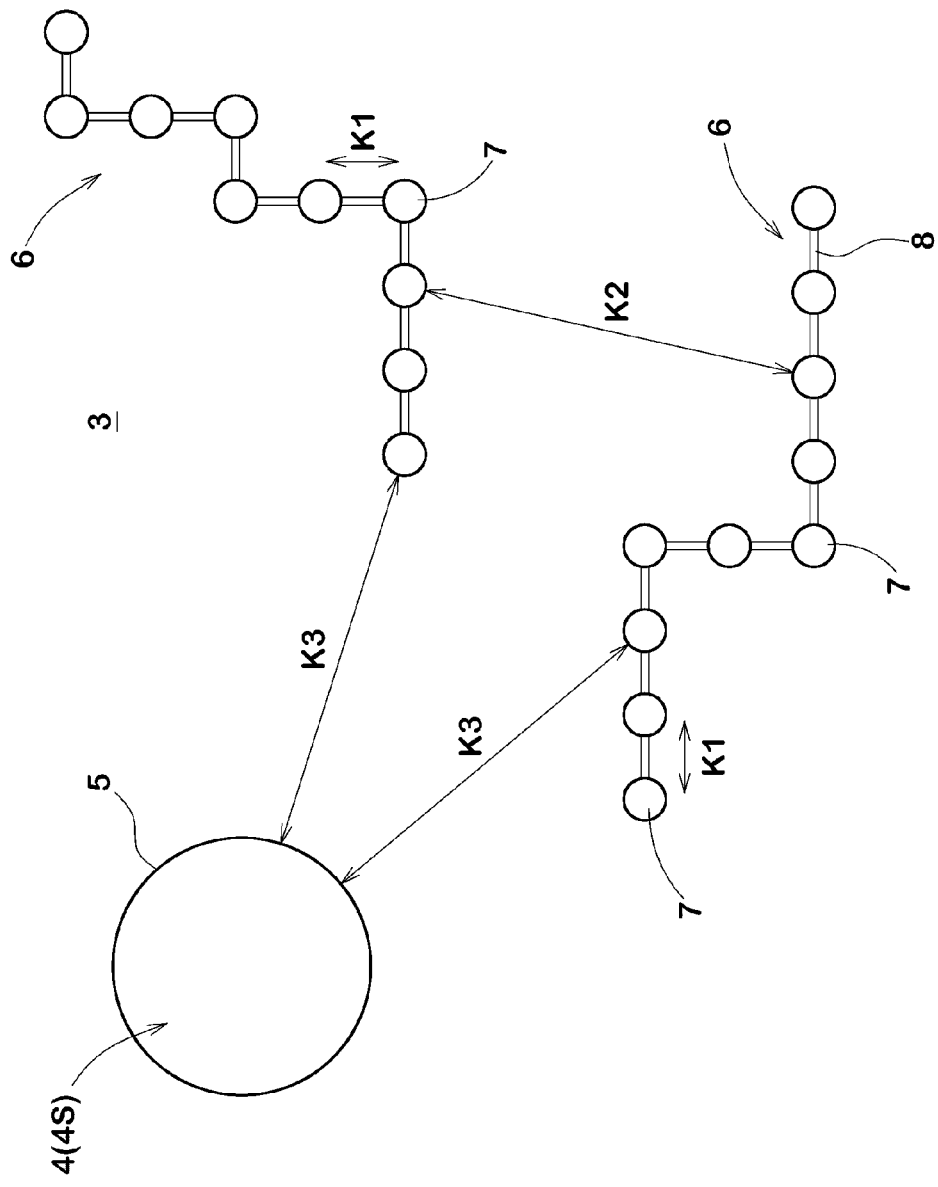
FIG. 4 is a diagram showing a filler model and polymer models.

As shown in FIG. 4, the filler model 4 is defined by a single filler segment 4s forcibly set in one domain 5 of the virtual space 3 divided into particles or a mesh. Namely, the filler segment 4s is constrained to the domain 5.

In this embodiment, the domain 5 is two-dimensional and defined as being of a circular shape. However, in the case of a three-dimensional filler model 4 where the filler segment 4s is also three-dimensional, it is preferable that the domain 5 is defined as being of a spherical shape.

In any case, data about the filler model 4 are stored in the computer 1.

In this embodiment, the filler segment 4s is treated as a minimum unit of a simulation based on the mean field theory (Flory-Huggins theory, etc.). Here, the mean field theory is a statistical thermodynamic theory for polymer solution used to mean-field approximate the interactions between a polymer and its surroundings.

* Process S3

In the process S3, a polymer model of each of macromolecular chains of the polymeric material is defined. As shown in FIG. 4, the polymer model 6 is defined by a plurality of polymer segments 7. As with the filler segment 4S, the polymer segment 7 is treated as a minimum unit of a simulation based on the mean field theory.

Between the polymer segments 7, a joining chain 8 is defined. For example, the length K1 of the joining chain 8 is set to a value corresponding to the mesh size of the system. Thus, the polymer model 6 is defined to have a two-dimensional straight-chain structure in which the relative distances between the polymer segments 7 are held stably.

A $\chi$ parameter K2 employed in the Flory-Huggins theory and relating to an interaction between a polymer segment 7 of a polymer model 6 and a polymer segment 7 of another polymer model 6 is set in a range of from 0.0 to 10.0 for example. As a result, between the polymer segments 7, a repulsive interaction and the intensity thereof are defined. Data about such the polymer segments 7 are stored in the computer 1.

* Process S4

In the process S4, the filler models 4 and the polymer models 6 are set in the virtual space 3 to have a predetermined volume fraction. For example, the volume fraction is set in a range of from 50% to 99%. In this embodiment, a pair of the filler models are set in the virtual space 3. Data about the concentration distribution of the polymer segments 7 of the polymer models 6 are stored in the computer 1.

* Process S5

In the process S5, a $\chi$ parameter K3 employed in the Flory-Huggins theory and relating to an interaction between a filler model 4 and a polymer model 6 is defined.

As shown in FIG. 4, $\chi$ parameters K3 are defined between the filler segments 4S and the polymer segments 7.

In this embodiment, the $\chi$ parameters K3 are set in a range of from 0.0 to 10.0. As a result, between the filler segment 4S and the polymer segment 7, a repulsive interaction and the intensity thereof are defined.

If the $\chi$ parameters K3 are more than 10.0, there is a possibility that, in the simulation based on the mean field theory, even if the arrangement of the filler models 4 and the polymer models 6 becomes close to their equilibrium state, the difference in the calculated energy from that calculated in the most recent calculation step is still large, and the computation can not be converged.

Therefore, preferably, the $\chi$ parameters K3 are set in a range of not more than 5.0. Such $\chi$ parameters K3 are stored in the computer 1.

* Simulation Process S6

In the simulation process S6, using the filler models 4 and the polymer models 6 set in the virtual space 3, a free energy in the virtual space 3 is calculated based on the mean field theory. Here, the free energy F is the Helmholtz free energy.

Figure 5:
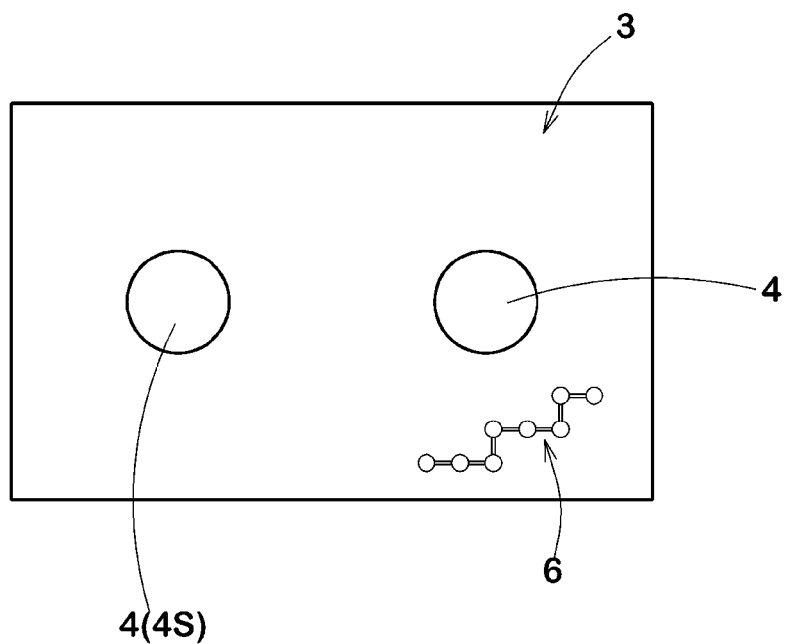
FIG. 5 is a diagram showing the filler models and the polymer models arranged in the virtual space.

As shown in FIG. 5, in the simulation based on the mean field theory, the free energy F of the equilibrium state of the virtual space including the filler models 4 and the polymer models 6, is calculated based on the SCF method (Self-Consistent Field Method) taking into account the entropy of the arrangement of the polymer models 6.

Such simulation based on the mean field theory can be implemented, for example, by the use of a simulation engine SUSHI built in a simulation system OCTA available from a website.

Figure 6:
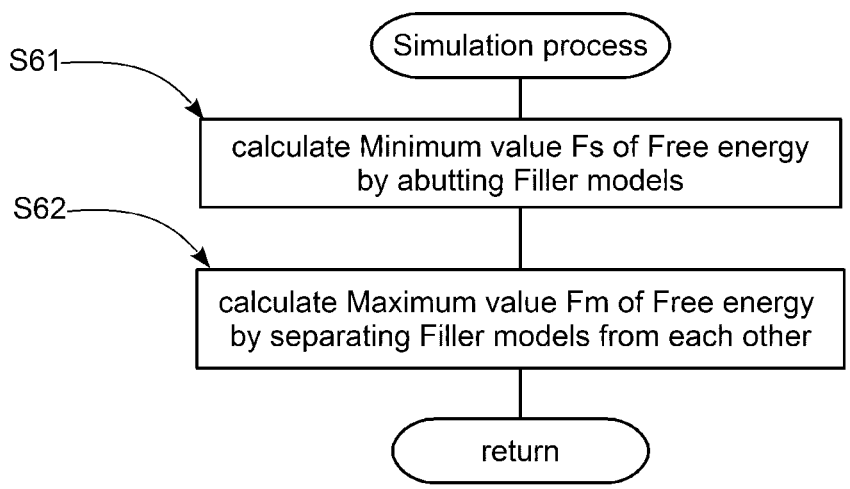
FIG. 6 is a flow chart of a simulation process of the calculating method.

FIG. 6 shows a flow chart of the simulation process S6.

** Process S61

In the process S61, by abutting the filler models 4, a minimum value Fs of the free energy F is calculated.

Figure 7A:
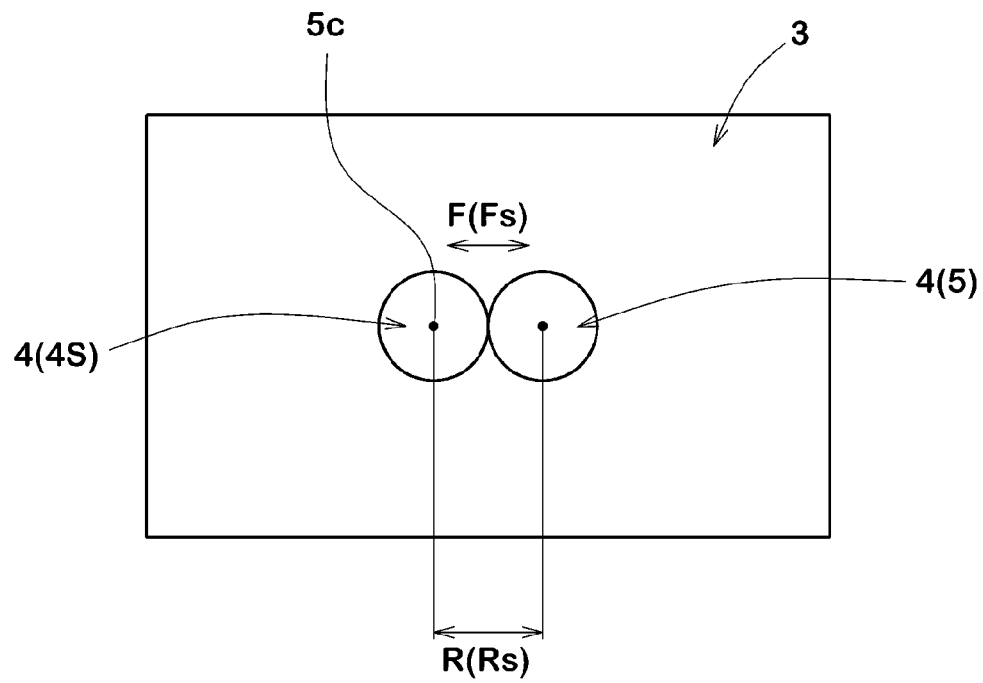
FIGS. 7(a) and 7(b) are diagrams showing the filler models in the virtual space for explaining processes for obtaining the minimum value Fs and the maximum value Fm of the free energy F in the virtual space.

As shown in FIG. 7(a), a pair of the filler models 4 are abutted each other, and the free energy F in the virtual space 3 under such abutting state of the pair of the filler models 4 is calculated.

In the abutting state of the pair of the filler models 4, the number of the polymer models 6 entering into the vicinity of the filler models 4 becomes least.

Therefore, a reduction in the entropy of the arrangement of the polymer models 6 is suppressed, and the free energy F in the virtual space 3 becomes a minimum value Fs.

Figure 7B:
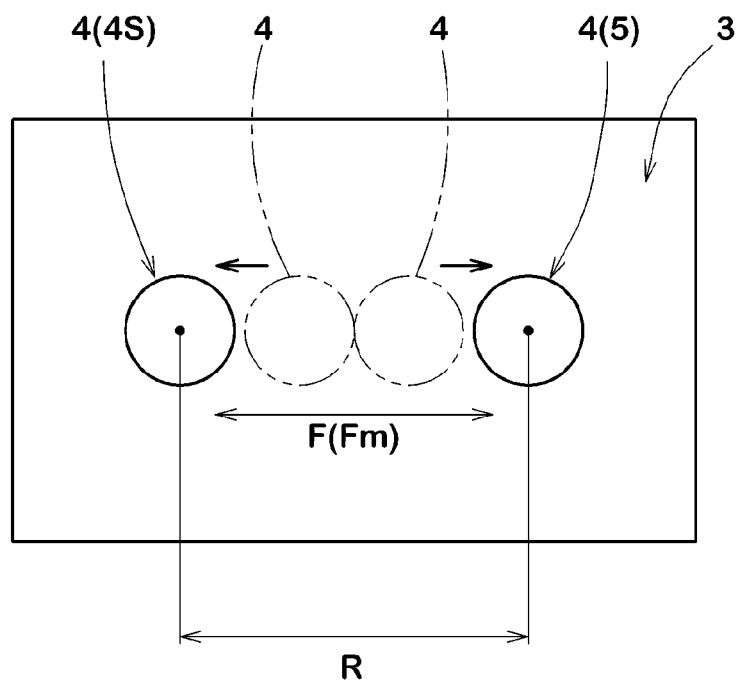

In FIG. 7(a) and FIG. 7(b), the polymer models 6 (shown in FIG. 5) are omitted for convenience sake.

Further, in the process S61, a distance R between the filler models 4 abutting each other, namely, the minimum distance Rs is obtained.

Here, the distance R between the filler models 4 is defined as the distance between the centers (centroids) 5c of the domains in which the filler segment 5 are disposed.

The obtained minimum value Fs of the free energy F and the obtained minimum distance Rs are stored in the computer 1.

** Process S62

In the process S62, by separating the abutting filler models 4 from each other, a maximum value Fm of the free energy F is calculated.

As shown in FIG. 7(b), while the distance R is gradually increased, the free energy F in the virtual space 3 is calculated.

Figure 8:
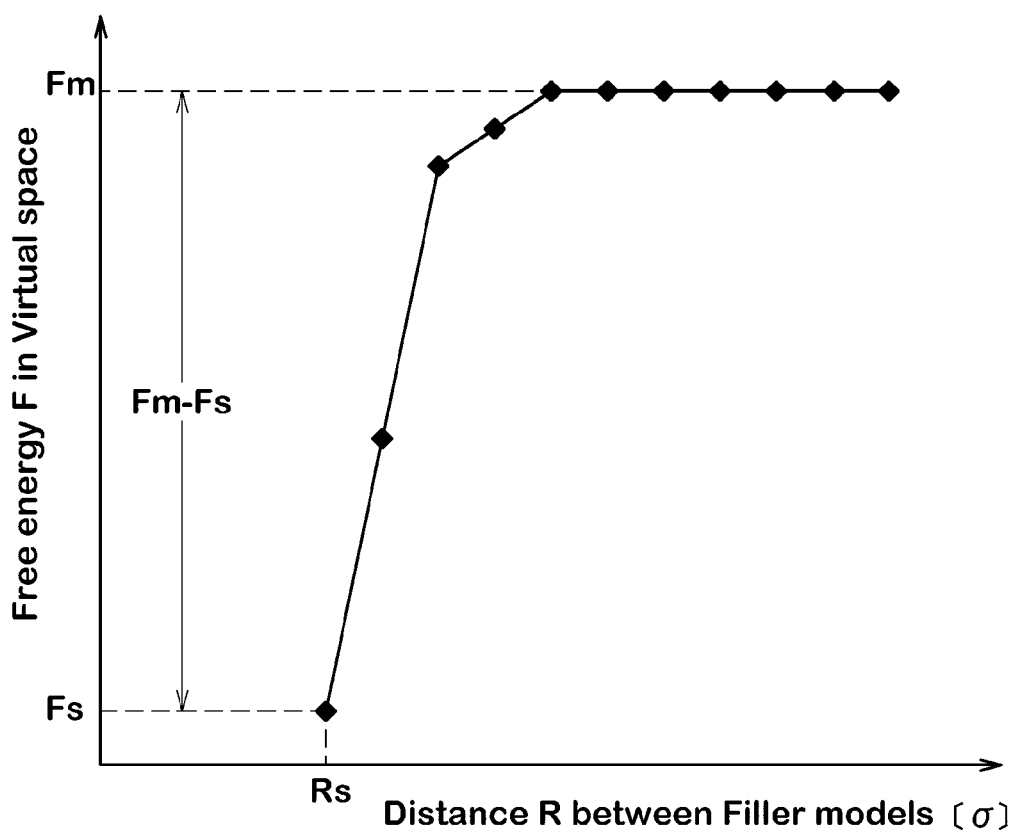
FIG. 8 is a graph showing a relationship between the free energy in the virtual space and the distance between the filler models.

The distances R and the free energy F of the entire system calculated at each distance R are stored in the computer 1. Thus, a relationship between the free energy F and the distance R can be obtained as shown in FIG. 8. As shown, with the increase in the distance R, the number of polymer models 6 entering into the vicinity of the filler models 4 is increased, and the free energy F in the virtual space 3 is increased. In this embodiment, the distance R between the filler models 4 is increased until the increment of the free energy becomes substantially zero to thereby obtain the maximum value Fm of the free energy F.

* Calculation Process S7

In the calculation process S7, by approximating the free energy F to the Lennard-Jones potential $U_{LJ}$, parameters of the Lennard-Jones potential $U_{LJ}$ are obtained by the computer 1. The Lennard-Jones potential $U_{LJ}$ is given by the following equation (1).

$$U_{LJ}(r_{ij}) = 4\varepsilon_{LJ}\left\{\left(\frac{\sigma_{LJ}}{r_{ij}}\right)^{12} - \left(\frac{\sigma_{LJ}}{r_{ij}}\right)^{6}\right\} \quad \text{Equation (1)}$$

wherein $r_{ij}$ is the distance between two filler models, $\varepsilon_{LJ}$ is a coefficient for the intensity of the potential between the filler models, and $\sigma_{LJ}$ corresponds to the diameter of the filler models.

Here, the distance $r_{ij}$ is the distance between the centers of the filler models.

In a molecular dynamics calculation, such Lennard-Jones potential $U_{LJ}$ is able to define a repulsive force acting between the filler models.

Figure 10:
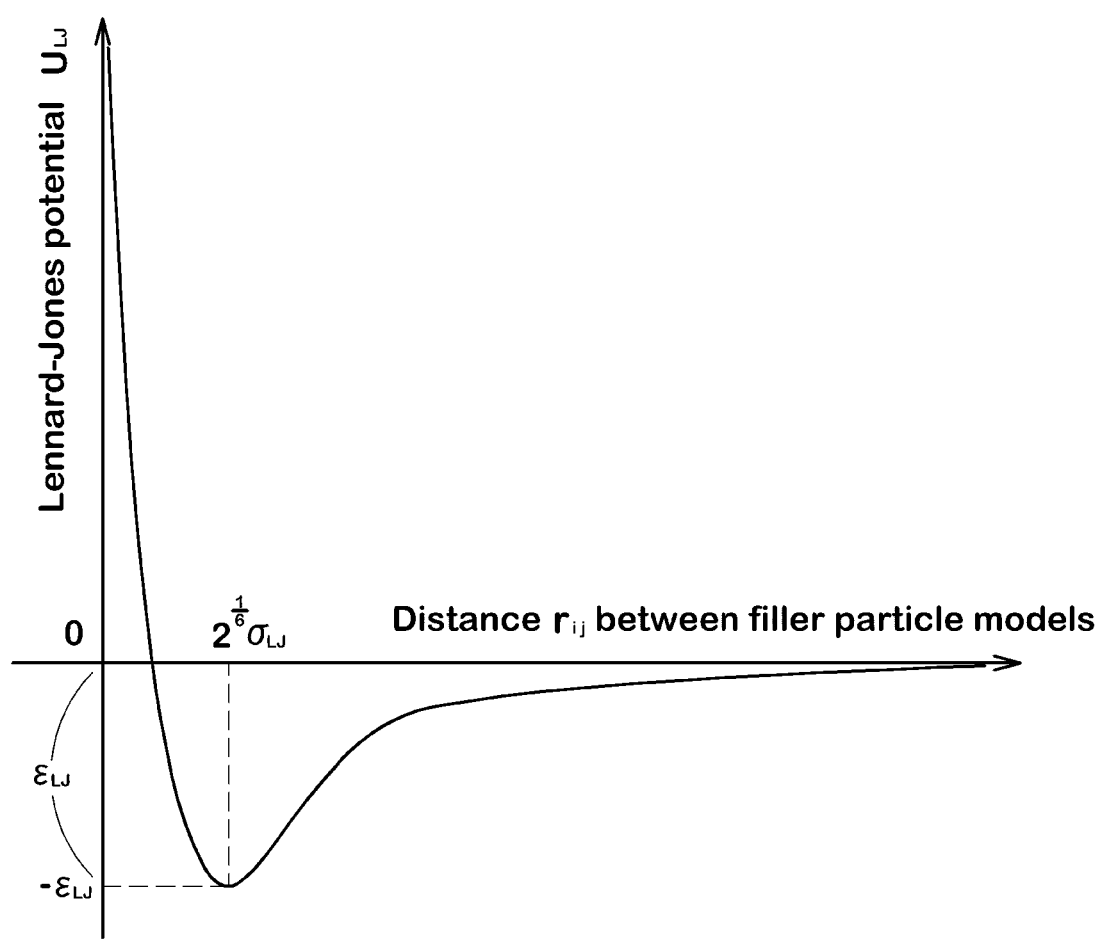
FIG. 10 is a graph showing a relationship between the Lennard-Jones potential and the distance between the filler models.

FIG. 10 is a graph showing a relationship between the Lennard-Jones potential $U_{LJ}$ and the distance $r_{ij}$.

when the distance $r_{ij}$ is $2^{1/6}\sigma_{LJ}$, the Lennard-Jones potential $U_{LJ}$ becomes a minimum value $-\varepsilon_{LJ}$.

when the pair of the filler models abut each other, the Lennard-Jones potential $U_{LJ}$ becomes minimized. Accordingly, the distance $r_{ij}$ when the pair of the filler models abut each other is $2^{1/6}\sigma_{LJ}$.

when the distance $r_{ij}$ is decreased toward zero from $2^{1/6}\sigma_{LJ}$, the Lennard-Jones potential $U_{LJ}$ increases to infinity and exerts a large repulsive force between the filler models.

when the distance $r_{ij}$ is increased from $2^{1/6}\sigma_{LJ}$, the Lennard-Jones potential $U_{LJ}$ gradually decreases and approaches to zero. This means that the influence of the Lennard-Jones potential $U_{LJ}$ is reduced with the increase in the distance $r_{ij}$.

The inventor found that, as a result of the above facts correlated, there is a correlation between the free energy F and the Lennard-Jones potential $U_{LJ}$.

In the present invention, by making a calculation based on the free energy F which varies according to the distance R, the parameters $\sigma_{LJ}$ and $\varepsilon_{LJ}$ of the Lennard-Jones potential $U_{LJ}$ is determined without the need for someone's intuition and experience.

Figure 11:
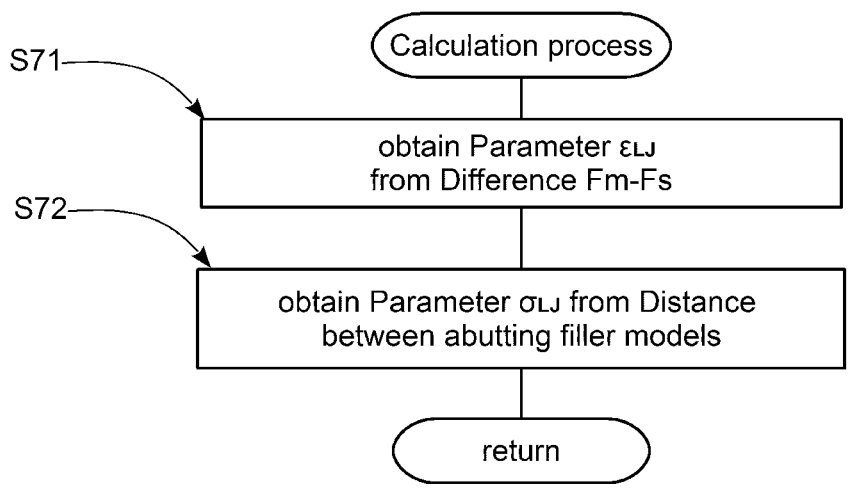
FIG. 11 is a flow chart of a calculation process of the calculating method.

FIG. 11 shows a flow chart of the calculation process S7 for obtaining the parameters $\sigma_{LJ}$ and $\varepsilon_{LJ}$.

** Process S71

In the process S71, the parameter $\varepsilon_{LJ}$ is obtained from the difference (Fm−Fs) between the maximum value Fm and the minimum value Fs of the free energy.

As shown in FIG. 10, when the distance $r_{ij}$ is in the range from $2^{1/6}\sigma_{LJ}$ to the higher, the difference between the maximum Lennard-Jones potential $U_{LJ}$ (0) and the minimum Lennard-Jones potential $U_{LJ}$ ($-\varepsilon_{LJ}$) is $\varepsilon_{LJ}$.

In the process S71, this difference ($\varepsilon_{LJ}$) is regarded as the same value as the difference (Fm−Fs).

Namely, $$\varepsilon_{LJ}=Fm-Fs \quad \text{Expression (2).}$$

Using this relational expression (2), the parameter $\varepsilon_{LJ}$ is obtained. The obtained parameter $\varepsilon_{LJ}$ is stored in the computer 1.

** Process S72

In the process S72, the parameter $\sigma_{LJ}$ is obtained from a distance between the filler models abutting each other.

As shown in FIG. 10, in the Lennard-Jones potential $U_{LJ}$, the distance $r_{ij}$ between the abutting filler models is $2^{1/6}\sigma_{LJ}$.

In the process S72, this distance $r_{ij}$ ($2^{1/6}\sigma_{LJ}$) is regarded as the same value as the minimum distance Rs.

Namely, $$2^{1/6}\sigma_{LJ}=Rs.$$

Accordingly, $$\sigma_{LJ}=Rs/2^{1/6} \quad \text{Expression (3).}$$

using this relational expression (3), the parameter $\sigma_{LJ}$ is obtained. The obtained parameter $\sigma_{LJ}$ is stored in the computer 1.

In the process S7, therefore, the parameters $\varepsilon_{LJ}$ and $\sigma_{LJ}$ of the Lennard-Jones potential can be obtained by the calculation based on the free energy F in the virtual space including the filler models as the analysis object. Thus, depending on the analysis object (filler models), the parameters $\varepsilon_{LJ}$ and $\sigma_{LJ}$ suitable for the analysis object can be obtained without the need for someone's intuition and experience, therefore, it is possible to perform the simulation with high accuracy.

* Process S8

In the process S8, a virtual space 13 including filler models 11 and polymer models 14 and corresponding to a micro-structural part of the polymeric material as the analysis object is newly defined, and a deformation calculation of the virtual space 13 is performed.

Figure 9:
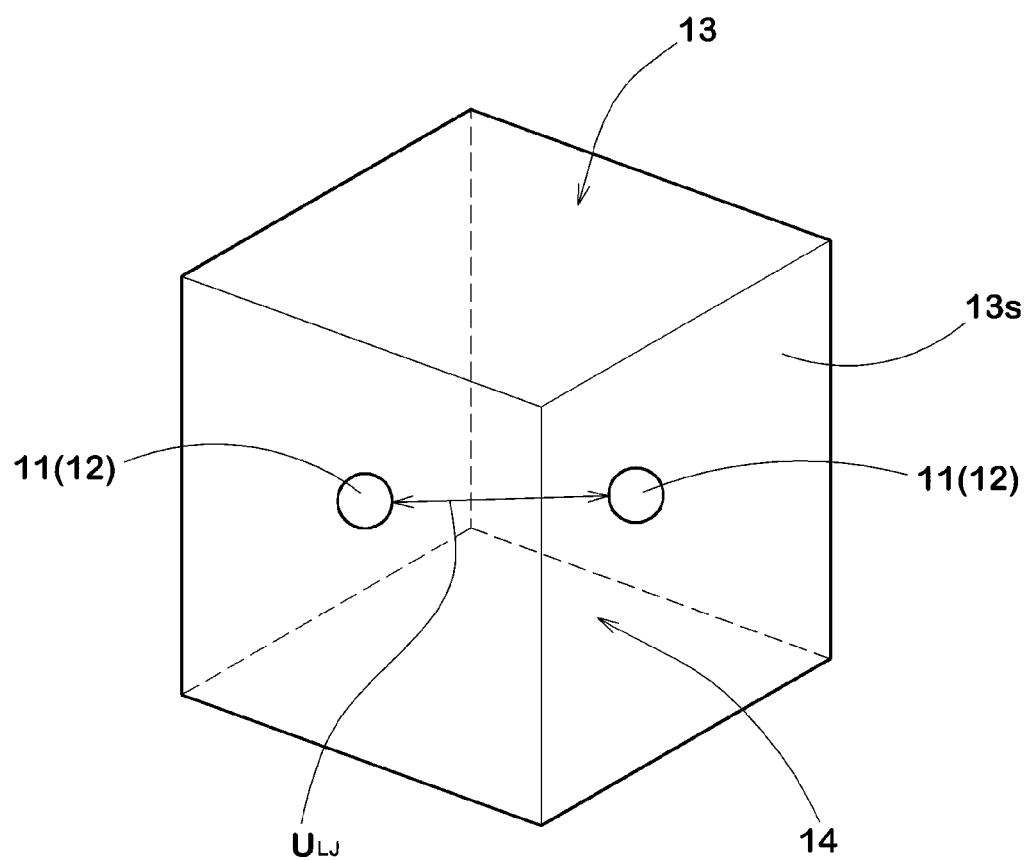
FIG. 9 is a diagram showing a virtual space used to perform a deformation calculation by defining the Lennard-Jones potential on filler models set in the virtual space.

In this embodiment, as shown in FIG. 9, the virtual space 13 is defined as a cube having three pairs of parallelly-opposed wall surfaces 13s. on each of the wall surfaces 13s, periodic boundary conditions are defined.

The filler models 11 are each defined by a single filler particle model 12 having a spherical shape and treated as a mass point of the equation of motion.

Between the filler models 11, there is defined the Lennard-Jones potential $U_{LJ}$ given by the above-mentioned equation (1) to which the values of the parameters $\epsilon_{LJ}$ and $\sigma_{LJ}$ obtained in the above-mentioned process S7 are assigned. The polymer models 14 which are of macromolecular chains of the polymeric material, are defined as a uniform fluid existing in the virtual space 13 between the filler models 11 and the wall surfaces 13s. on the polymer models 14, the viscosity of the polymeric material is defined.

Data about such virtual space 13 including the filler models 11 and the polymer models 14 are stored in the computer 1.

Then, the deformation calculation of the virtual space 13 is performed based on the Navier-stokes equation and the motion equation.

In this embodiment, the deformation calculation is performed until the strain becomes a value in a range of from 1 to 100, and a physical property (for example, viscosity, stress etc.) of the virtual space 13 is calculated.

The deformation rate of the virtual space 13 is set in a range of from about $10^{-6}$ to 1 $\sigma/\tau$.

On the assumption that the filler models 11 follow the classical dynamics, the Newton's equation of motion is employed.

The motions of the filler models 11 are tracked at regular time intervals.

During the deformation calculation, the number of the filler models in the virtual space, and the temperature and the volume of the virtual space are kept constant.

For example, such deformation calculation can be implemented by the use of a simulation software KAPSEL available from the same website as the above-mentioned simulation system OCTA.

As explained above, in the process S8, the parameters $\epsilon_{LJ}$ and $\sigma_{LJ}$ of the Lennard-Jones potential $U_{LJ}$ are set to the values of the parameters $\epsilon_{LJ}$ and $\sigma_{LJ}$ obtained by the calculation process S7.

* Process S9

In the process S9, the computer 1 judges whether the physical property of the virtual space 13 is acceptable or not.

If not acceptable, the conditions of the filler models 11 and the polymer models 14 are changed.—Process S11

Then, the processes S1 to S9 are repeated.

If acceptable, based on the conditions of the filler models 11 and the polymer models 14, the polymeric material including the filler is actually produced.—Process S10

Thus, in this embodiment, the conditions of the filler models 11 and the polymer models 14 are changed until the physical property of the virtual space 13 becomes acceptable, therefore, the polymeric material with desired performance can be developed efficiently.

Confirmation Test

According to the procedure shown in FIG. 2, the parameters $\epsilon_{LJ}$ and $\sigma_{LJ}$ were obtained, and the deformation calculation of the virtual space was performed in order to obtain the viscosity of the polymeric material including the filler. The obtained viscosity was compared with the actual measurement value. As a result, it was confirmed that the obtained viscosity well corresponds to the actual measurement value. The conditions and parameters used in the calculations are as follows.

In the process for obtaining the parameters $\epsilon LJ$ and $\alpha LJ$, virtual space 3:
  L1: 30 $\sigma$
  L2: 60 $\sigma$
Filler Model 4:
  Number in the virtual space: 2
  Diameter: 6 $\sigma$
Polymer Model 6:
  volume fraction in the virtual space: 80%
  Chain length of polymer segment: 50 (Linear molecule)
  Diameter of polymer segment: 1 $\sigma$
  $\chi$ parameter K2 between polymer models: 0.0
  $\chi$ parameter K3 between filler model and polymer model: 3.0.
In the deformation calculation,
virtual space 13: cube
  L1 of each side: 300 $\sigma$
Filler model 11:
  Number in the virtual space: 100
  Diameter: 6 $\sigma$
Polymer model 14:
  Viscosity: 1.0 $\eta$
  Absolute temperature: 1.0$\epsilon$/kB.

The invention claimed is:

1. A computer-implemented simulation method for evaluating properties of a polymeric material and filler particles, the method comprising:
   calculating an interaction potential between the filler particles in the polymeric material, comprising:
      a process in which a filler model of each of the filler particles is defined,
      a process in which a polymer model of each of macromolecular chains of the polymeric material is defined,
      a process in which the filler models and the polymer models are arranged in a predetermined virtual space, wherein the filler models are a pair of filler models each having a diameter,
      a process in which a free energy in the virtual space is calculated based on a mean field theory, and which comprises:
         a step in which, by abutting the filler models, a minimum value (Fs) of the free energy is calculated, and
         a step in which, by separating the filler models from each other, a maximum value (Fm) of the free energy is calculated,
      a process in which, by approximating the free energy to a Lennard-Jones potential ($U_{LJ}$), parameters of the Lennard-Jones potential are obtained,
   wherein:
   the Lennard-Jones potential ($U_{LJ}$) is given by the following equation (1):

$$U_{LJ}(r_{ij}) = 4\epsilon_{LJ}\left\{\left(\frac{\sigma_{LJ}}{r_{ij}}\right)^{12} - \left(\frac{\sigma_{LJ}}{r_{ij}}\right)^{6}\right\}, \quad \text{Equation (1)}$$

wherein
   $r_{ij}$ is a distance between the pair of filler models,
   $\epsilon_{LJ}$ is a coefficient for an intensity of a potential between the pair of filler models, and
   $\sigma_{LJ}$ corresponds to the diameter of each of the pair of filler models,
   said parameters of the Lennard-Jones potential are the $\epsilon_{LJ}$ and $\sigma_{LJ}$,
   the process for obtaining said parameters comprises:
      a step in which the parameter $\epsilon_{LJ}$ is obtained from the difference between the maximum value (Fm) and the minimum value (Fs) of the free energy, and
      a step in which the parameter $\sigma_{LJ}$ is obtained from a distance between the filler models which abut each other in order to calculate the minimum value (Fs) of the free energy,
   the method further comprises:

a process for newly defining a virtual space which includes filler models and polymer models and corresponds to a micro-structural part of the polymeric material, a process for performing a deformation calculation on the newly defined virtual space to calculate a physical property thereof, wherein, between the filler models, the Lennard-Jones potential ($U_{LJ}$) given by the equation (1) is defined, to which the obtained values of the parameters $\varepsilon_{LJ}$ and $\sigma_{LJ}$ are assigned, and a process for judging whether the physical property is acceptable or not by comparing with a given criterion, and producing the polymeric material including the filler particles based on conditions of the filler models and the polymer models in the newly defined virtual space, when the physical property is acceptable by comparing with the given criterion.

2. The method according to claim 1, wherein

Flory-Huggins theory is employed as the mean field theory, and a $\chi$ parameter employed in the Flory-Huggins theory and relating to an interaction between the filler model and the polymer model is set in a range of from 0.0 to 10.0.

* * * * *